United States Patent
Mann et al.

(10) Patent No.: US 8,670,524 B2
(45) Date of Patent: Mar. 11, 2014

(54) ARRANGEMENT OF ANALYZER MEASURING WINDOW

(75) Inventors: Kari Mann, Espoo (FI); Christian Von Alfthan, Espoo (FI)

(73) Assignee: Outotec Oyj, Espoo (FI)

( * ) Notice: Subject to any disclaimer, the term of this patent is extended or adjusted under 35 U.S.C. 154(b) by 293 days.

(21) Appl. No.: 13/322,436

(22) PCT Filed: May 24, 2010

(86) PCT No.: PCT/FI2010/050418
§ 371 (c)(1),
(2), (4) Date: Nov. 23, 2011

(87) PCT Pub. No.: WO2010/136647
PCT Pub. Date: Dec. 2, 2010

(65) Prior Publication Data
US 2012/0093300 A1 Apr. 19, 2012

(30) Foreign Application Priority Data
May 26, 2009 (FI) .................................... 20090209

(51) Int. Cl.
*H01J 5/18* (2006.01)
(52) U.S. Cl.
USPC ......................................... 378/140; 378/161
(58) Field of Classification Search
USPC .............. 378/44, 45, 119, 121, 140, 161, 208
See application file for complete search history.

(56) References Cited

U.S. PATENT DOCUMENTS

| | | | |
|---|---|---|---|
| 3,354,308 | A | 11/1967 | Engel |
| 3,443,092 | A | 5/1969 | Carr-Brion |
| 3,562,535 | A | 2/1971 | Leger, Jr. |
| 5,832,053 | A | 11/1998 | Field |
| 6,301,335 | B1 | 10/2001 | Von Alfthan |

FOREIGN PATENT DOCUMENTS

| | | |
|---|---|---|
| GB | 1109276 A | 4/1968 |
| GB | 2191285 A | 12/1987 |

OTHER PUBLICATIONS

Kenneth Gustafsson, International Search Report for PCT/FI2010/050418, Sep. 17, 2010.

*Primary Examiner* — Courtney Thomas
(74) *Attorney, Agent, or Firm* — Chernoff Vilhauer McClung & Stenzel LLP

(57) ABSTRACT

The invention relates to an arrangement of a measuring window in a continuously operated X-ray analyzer (1), said analyzer being is used particularly for analyzing elemental contents in solid, liquid or slurry-like materials; which measuring window (2) separates the sampling space (3) containing the sample material to be measured and the measurement space (4) containing the measuring probe (11), and is sealed by a lid structure (6) arranged in the sampling space, said lid structure defining the measurement aperture (7) of the sampling space, in which case the lid structure defining the measurement aperture of the sampling space is provided with a sealing surface (8) of the measuring window, so that said surface is at least partly planar and at least partly curved.

8 Claims, 2 Drawing Sheets

ARRANGEMENT OF ANALYZER MEASURING WINDOW

Figure 1:
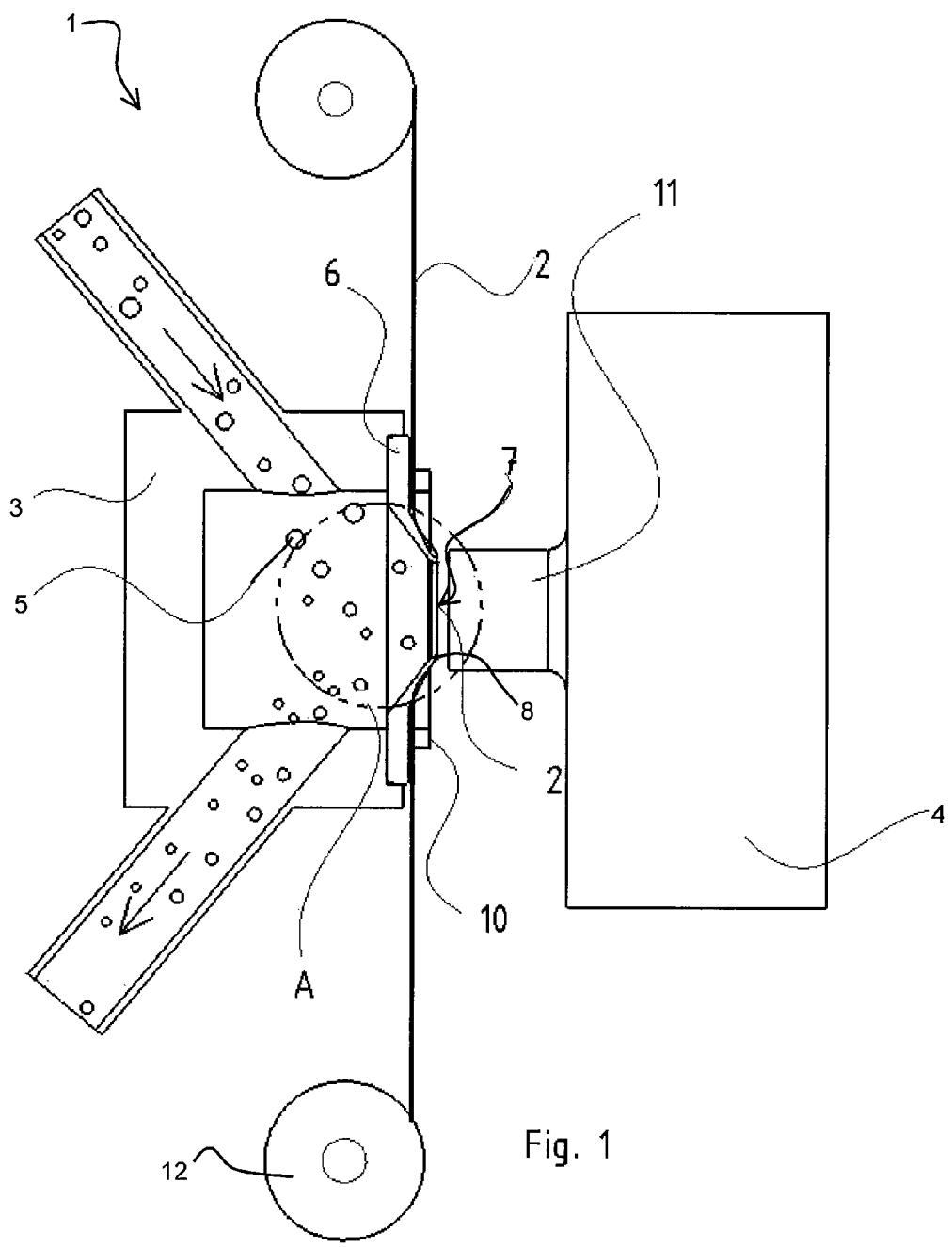

This is a national stage application filed under 35 USC 371 based on International Application No. PCT/FI2010/050418, filed May 24, 2010, and claims priority under 35 USC 119 of Finnish Patent Application No. FI20090209 filed May 26, 2009.

The invention relates to an arrangement of a measuring window in a continuously operated X-ray analyzer, defined in the preamble of claim 1.

When analyzing the elemental contents of solid, liquid or slurry-like materials, the sample to be analyzed is located in a specific measurement space. Typically the employed analyzing method is an X-ray fluorescence method, where the samples to be analyzed generate, by means of radiation quanta obtained from an X-ray source, radiation that is characteristic to various elements. The intensity of this characteristic radiation is dependent on the elemental content in the sample, and therefore the radiation intensity is measured by a detector that is, together with the X-ray source, installed at the measuring probe of the analyzer. In a continuously operated measurement, the measuring probe is placed in a separate measurement space and it is insulated from the sample by a measuring window permeable to X-rays. The measuring window is often made of thin plastic material, which is stretched as part of the wall. It must be leak-proof and endure the possible pressure prevailing in the sampling chamber. In order to perform the measurement of radiation intensities as accurately as possible, the geometrical position of the measuring window must remain essentially the same, and the measuring window is not allowed to remarkably bulge owing to the effect of changes in the sampling space pressure. In continuous measurement, the measuring window is worn owing to the sample flow, or solid material is precipitated thereon, which causes errors in analysis, thus essentially weakening the accuracy of the measurement. The measuring window must be replaced from time to time, which in practice is the most remarkable maintenance operation with analyzers, and thus affects the operation and maintenance expenses.

In the prior art, there is known the publication FI 110819, which relates to an analyzer measuring window and a method for installing said window. According to the arrangement set forth in the publication, the measuring window can be moved with respect to a measurement aperture provided in the wall of the measurement space containing the measuring probe of the analyzer and a sample aperture arranged in the sampling space.

Moreover, as an example of the prior art, there is known the patent publication U.S. Pat. No. 5,048,325, which describes a measurement cell for defining the contents of components contained in slurries that are in a flowing motion. According to said publication, the inlet pipe of the analyzer is set in an inclined position with respect to the level of the measuring window, and the invention relates to an advantageous way for directing the slurry jet towards the measuring window.

Yet another problem is how to make the area of the measuring window so leak-proof that it endures the overpressure prevailing in the sampling space without leaking liquid or slurry. The planar shape of the measuring window must be maintained, in order to prevent any disturbance in the accuracy of the measurement result. Moreover, the materials employed in the vicinity of the measuring window must not disturb the accuracy of the measurement result.

The object of the invention is to eliminate drawbacks of the prior art and to realize a new and more reliable way for sealing the measuring window in the sampling space of an analyzer during measurement.

The invention relates to an arrangement of a measuring window in a continuously operated X-ray analyzer, which analyzer is particularly used when analyzing the elemental contents of solid, liquid or slurry-like materials, said measuring window separating the sample space containing the sample material to be measured, and the measurement space containing the measuring probe, and it is sealed by a lid structure arranged in the sampling space, which lid structure outlines the measurement aperture of the sampling space, so that the lid structure outlining the measurement aperture of the sampling space is provided with a surface sealing the measuring window, in which case the surface is at least partly planar and at least partly curved. By applying the lid structure shape according to the invention, there is achieved an advantageous arrangement, in which the measuring window remains tightly in place throughout the measuring operation. According to an embodiment of the invention, the sealing surface is at least partly vertical. According to an embodiment of the invention, the sealing surface is at least partly conical. The arrangement of a measuring window according to the invention strictly separates the measuring probe from the sample and effectively prevents the sample from flowing out of the sampling space.

According to the invention, the shape of the surface that outlines the measurement aperture of the sampling space in the lid structure is a truncated cone. This is an advantageous shape with respect to the flowing of the sample material contained in the sampling space. According to an embodiment of the invention, the radius of curvature at the curved section of the sealing surface is preferably 0.3-1.0 millimeters. Now the diaphragm serving as the measuring window is advantageously set in connection with the measuring window, thus sealing the sampling space. According to a preferred embodiment of the invention, the width of the sealing surface of the lid structure is preferably larger than 1 millimeter. Now the sampling space wall preferably has an allowance for wearing, with respect to the wearing caused by the flowing sample. Wearing takes place in continuous measurement of a sample, owing to the flowing motion of the sample.

According to an embodiment of the invention, there is an annular sealing element in the space left in between the measurement space and the sampling space. Said sealing element locks the measuring window tightly in connection with the lid structure for the duration of the measuring operation.

According to the invention, the lid structure is made of a wear-resistant ceramic material, such as silicon carbide. This material is advantageously durable, and there are achieved advantages in material expenses, because the lid structure need not be replaced very often owing to wearing. Moreover, the material is good, because it does not cause errors in X-ray measurement results, and it endures radiation without damages.

In an arrangement according to the invention, the measuring window is advantageously sealed against the lid structure, so that leaks do not occur during continuous measurement.

Figure 2:
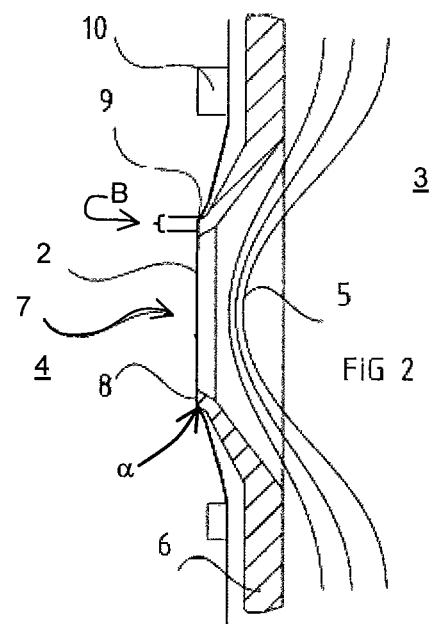
Figure 3:
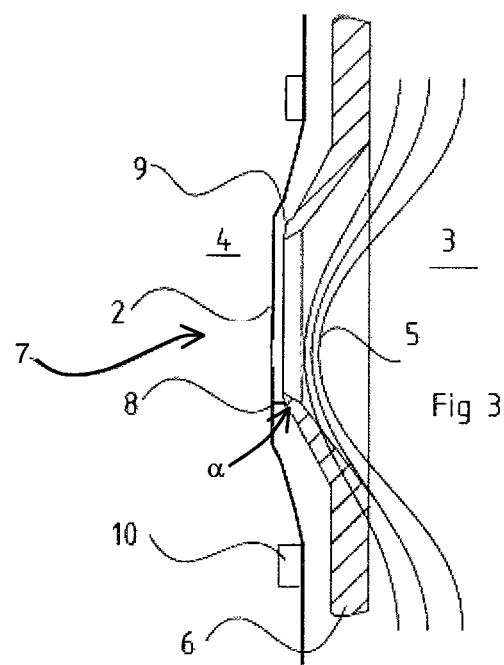

The invention is described in more detail below, with reference to preferred embodiments and to the appended drawing, where FIG. 1 illustrates a preferred embodiment of the invention, shown as a schematical drawing in principle, FIG. 2 illustrates an embodiment of the invention, and FIG. 3 illustrates an embodiment of the invention.

FIG. 1 illustrates an arrangement of a measuring window 2 in a continuously operated X-ray analyzer 1 according to the invention, said analyzer being used particularly when analyzing elemental contents in solid, liquid or slurry-like materials. FIG. 1 illustrates the analyzer 1 in a situation where a measurement is going on, in which case the sampling space 3 and the measurement space 4 are arranged together. In a measurement situation, the sampling space 3 containing the sample 5 to be measured, and the measurement space 4 of the analyzer, are insulated from each other by a flexible material permeable to X-rays, such as a measuring window 2 made of plastic film. The measurement space 4 contains at least a measuring probe 11 and the X-ray source of the detector. In the sampling space 3, the samples 5 to be analyzed generate, by means of radiation quanta obtained from the X-ray source, radiation characteristic to various elements. The analyzer 1 includes a lid structure 6 of the sampling space according to the invention, which lid structure is in a measurement situation in contact with the measuring window, so that liquid tightness in the sampling space 3 containing the sample material 5 to be measured is maintained. The measuring window 2 can be moved in the space left between the sampling space 3 and the measurement space 4, in between separate measurement situations, by means of suitable transfer elements, such as rollers 12, when the measuring window 2 should be replaced by a new one either manually or automatically. The replacing of the measuring window is carried out so that it disturbs the measurement operations of the analyzer as little as possible. The measuring window 2 is stretched in the measurement aperture 7 outlined by the lid structure 6 of the sampling space 3, so that it forms a smooth surface in the aperture.

FIG. 2 illustrates an embodiment of the invention. FIG. 2 is an enlargement of point A in FIG. 1. In the lid structure 6 outlining the measurement aperture 7 of the sampling space 3 of an analyzer 1 according to the invention, there is arranged a sealing surface 8 of the measuring window, shown in FIG. 2, so that said surface 8 is at least partly planar and at least partly curved. According to the embodiment of FIG. 2, the sealing surface 8 is at least partly vertical. The radius of curvature α of the curved section 9 of the sealing surface 8 is preferably 0.3-1.0 millimeters, in which case the measuring window 2 is set tightly in the lid structure 6. Thus the measuring window 2 is arranged tightly in connection with the measurement aperture 7, so that there is achieved a high sealing surface pressure, and when being tightened, the measuring window may slide against the measurement aperture. According to the invention, the surface that outlines the measurement aperture 7 in the lid structure of the sampling space 3 has the shape of a truncated cone, in which case the shape of the measurement aperture 7 is preferably round at the point where the measuring window is set against the measurement aperture. The diaphragm used as the measuring window is clamped by a sealing element 10 as part of the lid structure, so that the sampling space becomes leak-proof. The sealing element 10 is formed of at least one annular sealing element, which can be fitted to fix the measuring window in connection with the lid structure 6, so that the measuring window 2 remains, during the measurement operation, essentially immobile and leak-proof. According to the invention, the width B of the sealing surface 8 is preferably larger than 1 millimeters, in which case there is left sufficiently wearing surface in that wall of the measurement aperture 7 that is located on the side of the sampling space, for the wearing caused by the sample material 5 contained in the sampling space 3. When the material employed in the lid structure according to the invention is a ceramic material, such as silicon carbide, separate sealing materials are not needed for sealing the measuring window.

FIG. 3 shows an enlargement of point A in FIG. 1. FIG. 3 illustrates, as an embodiment of the invention, an analyzer lid structure 6, where the sealing surface 8 is partly conical. In FIG. 3, the measuring window 2 is represented so that it is not in contact with the lid structure 6. In a measurement situation, the measuring window is in contact with the lid structure 6, in which case it is set against the sealing surface 8. Now the grains contained in the sample 5 are effectively prevented from getting access to the space left in between the measuring window and the lid structure during measurement.

The invention is not restricted to the above described embodiments only, but many modifications are possible within the scope of the inventive idea defined in the claims.

The invention claimed is:

1. An arrangement of a measuring window in a continuously operated X-ray analyzer (1), said analyzer being used particularly when analyzing elemental contents in solid, liquid or slurry-like materials, which measuring window (2) separates a sampling space (3) containing a sample material to be measured and a measurement space (4) containing a measuring probe (11), and is sealed onto a lid structure (6) arranged in the sampling space, said lid structure (6) defining a measurement aperture (7) of the sampling space, characterized in that the lid structure (6), made of ceramic material, defining the measurement aperture (7) of the sampling space, is provided with a sealing surface (8) of the measuring window, said sealing surface (8) surrounding the measurement aperture (7) and being at least partly planar and having a curved section, the sealing surface (8) being elevated with respect to a surface of the lid structure (6) surrounding the sealing surface (8).

2. An arrangement of a measuring window according to claim 1, characterized in that the planar part of the sealing surface (8) is at least partly vertical.

3. An arrangement of a measuring window according to claim 1, characterized in that the planar part of the sealing surface (8) is at least partly conical.

4. An arrangement of a measuring window according to claim 1, characterized in that the shape of the lid structure defining the measurement aperture of the sampling space is a truncated cone.

5. An arrangement of a measuring window according to claim 1, characterized in that the radius of curvature (α) of the curved section (9) of the sealing surface (8) is preferably 0.3-1.0 millimeters.

6. An arrangement of a measuring window according to claim 1, characterized in that the width (B) of the sealing surface (8) of the lid structure is preferably larger than 1 millimeter.

7. An arrangement of a measuring window according to claim 1, characterized in that in the space left between the measurement space and the sampling space, there is arranged an annular sealing element (10).

8. An arrangement of a measuring window according to claim 1, characterized in that the lid structure is made of ceramic material, such as silicon carbide.

\* \* \* \* \*